(12) United States Patent
Saadat et al.

(10) Patent No.: US 7,918,869 B2
(45) Date of Patent: Apr. 5, 2011

(54) METHODS AND APPARATUS FOR PERFORMING ENDOLUMINAL GASTROPLASTY

(75) Inventors: Vahid Saadat, Saratoga, CA (US); Desmond H. Birkett, Boston, MA (US); Eugene G. Chen, Carlsbad, CA (US)

(73) Assignee: USGI Medical, Inc., San Clemente, CA (US)

( * ) Notice: Subject to any disclaimer, the term of this patent is extended or adjusted under 35 U.S.C. 154(b) by 828 days.

(21) Appl. No.: 10/841,415

(22) Filed: May 7, 2004

(65) Prior Publication Data

US 2005/0251158 A1    Nov. 10, 2005

(51) Int. Cl.
*A61B 17/08* (2006.01)
*A61B 1/00* (2006.01)

(52) U.S. Cl. .................................. 606/153; 600/104

(58) Field of Classification Search .................. 606/153, 606/108, 191, 192, 194, 213; 600/37, 104, 600/107, 114, 129, 139, 144, 146, 153, 235, 600/585, 156; 604/22, 264, 270, 271; 128/898
See application file for complete search history.

(56) References Cited

U.S. PATENT DOCUMENTS

| | | | |
|---|---|---|---|
| 616,672 A | 12/1898 | Kelling | |
| 1,814,791 A | 7/1931 | Ende | |
| 2,201,610 A | 5/1940 | Dawson, Jr. | |
| 2,413,142 A | 12/1946 | Jones et al. | |
| 2,510,198 A | 6/1950 | Tesmer | |
| 2,533,494 A | 12/1950 | Mitchell, Jr. | |
| 3,060,972 A | 10/1962 | Sheldon | |
| 3,096,962 A | 7/1963 | Johannes | |
| 3,150,379 A | 9/1964 | Brown | |
| 3,162,214 A | 12/1964 | Bazinet, Jr. | |
| 3,166,072 A | 1/1965 | Sullivan, Jr. | |
| 3,168,274 A | 2/1965 | Street | |
| 3,430,662 A | 3/1969 | Guarnaschelli | |
| 3,494,006 A | 2/1970 | Brumlik | |
| 3,546,961 A | 12/1970 | Marton | |
| 3,551,987 A | 1/1971 | Wilkinson | |
| 3,643,653 A * | 2/1972 | Takahashi et al. | 600/129 |
| 3,646,615 A | 3/1972 | Ness | |

(Continued)

FOREIGN PATENT DOCUMENTS

EP    0 480 428 A2    4/1992

(Continued)

OTHER PUBLICATIONS

Bluett et al., "Experimental Evaluation of Staple Lines in Gastric Surgery," *Arch. Surg.*, vol. 122, (Jul. 1987), pp. 772-776.

(Continued)

*Primary Examiner* — Julian W Woo
(74) *Attorney, Agent, or Firm* — Charles C. Fowler; Levine Bagade Han LLP

(57) ABSTRACT

The present invention provides methods and apparatus for endoluminally performing gastroplasty. In one variation, the apparatus comprises a sizing tube, and a steerable guide that may be reversibly disposed within the sizing tube. In another variation, the sizing tube and steerable guide are integrated into a single device. In one method of utilizing the apparatus, a pouch is endoluminally formed within a patient's stomach, thereby partitioning or reducing the stomach and restricting the flow of food therethrough. The pouch may form a Vertical Banded Gastroplasty or Magenstrasse and Mill in an endoluminal fashion. Advantageously, the sizing tube or steerable guide may be used to properly size the endoluminal pouch.

30 Claims, 7 Drawing Sheets

U.S. PATENT DOCUMENTS

| | | | |
|---|---|---|---|
| 3,664,345 A | 5/1972 | Dabbs et al. | |
| 3,753,438 A | 8/1973 | Wood et al. | |
| 3,858,578 A | 1/1975 | Milo | |
| 3,867,944 A | 2/1975 | Samuels | |
| 3,874,388 A | 4/1975 | King et al. | |
| 3,910,281 A | 10/1975 | Kletschka et al. | |
| 3,913,565 A * | 10/1975 | Kawahara | 600/585 |
| 3,974,834 A | 8/1976 | Kane | |
| 3,976,079 A | 8/1976 | Samuels et al. | |
| 4,007,743 A | 2/1977 | Blake | |
| 4,036,218 A | 7/1977 | Yamashita et al. | |
| 4,054,128 A | 10/1977 | Seufert et al. | |
| 4,060,089 A | 11/1977 | Noiles | |
| 4,069,825 A | 1/1978 | Akiyama | |
| 4,245,624 A | 1/1981 | Komiya | |
| 4,366,810 A | 1/1983 | Slanetz | |
| 4,367,746 A | 1/1983 | Derechinsky | |
| 4,414,720 A | 11/1983 | Crooms | |
| 4,462,402 A | 7/1984 | Burgio et al. | |
| 4,474,174 A * | 10/1984 | Petruzzi | 600/104 |
| 4,494,531 A | 1/1985 | Gianturco | |
| 4,532,926 A | 8/1985 | O'holla | |
| 4,534,350 A | 8/1985 | Golden et al. | |
| 4,548,202 A | 10/1985 | Duncan | |
| 4,586,503 A | 5/1986 | Kirsch et al. | |
| 4,592,339 A | 6/1986 | Kuzmak et al. | |
| 4,592,356 A | 6/1986 | Gutierrez | |
| 4,595,007 A | 6/1986 | Mericle | |
| 4,601,283 A | 7/1986 | Chikama | |
| 4,610,250 A | 9/1986 | Green | |
| 4,648,733 A | 3/1987 | Merkt | |
| 4,655,257 A | 4/1987 | Iwashita | |
| 4,669,473 A | 6/1987 | Richards et al. | |
| 4,705,040 A | 11/1987 | Mueller et al. | |
| 4,711,002 A | 12/1987 | Kreeger | |
| 4,724,840 A | 2/1988 | McVay et al. | |
| 4,750,492 A | 6/1988 | Jacobs | |
| 4,765,335 A | 8/1988 | Schmidt et al. | |
| 4,832,055 A | 5/1989 | Palestrant | |
| 4,841,888 A | 6/1989 | Mills et al. | |
| 4,841,949 A * | 6/1989 | Shimizu et al. | 600/107 |
| 4,873,976 A | 10/1989 | Schreiber | |
| 4,890,615 A | 1/1990 | Caspari et al. | |
| 4,923,461 A | 5/1990 | Caspari et al. | |
| 4,929,240 A | 5/1990 | Kirsch et al. | |
| 4,949,927 A | 8/1990 | Madocks et al. | |
| 4,957,498 A | 9/1990 | Caspari et al. | |
| 5,032,127 A | 7/1991 | Frazee et al. | |
| 5,035,692 A | 7/1991 | Lyon et al. | |
| 5,037,433 A | 8/1991 | Wilk et al. | |
| 5,041,129 A | 8/1991 | Hayhurst et al. | |
| 5,059,201 A | 10/1991 | Asnis | |
| 5,088,979 A | 2/1992 | Filipi et al. | |
| 5,100,418 A | 3/1992 | Yoon et al. | |
| 5,108,420 A | 4/1992 | Marks | |
| 5,122,136 A | 6/1992 | Guglielmi et al. | |
| 5,123,914 A | 6/1992 | Cope | |
| RE34,021 E | 8/1992 | Mueller et al. | |
| 5,156,046 A | 10/1992 | Tanimoto et al. | |
| 5,201,746 A | 4/1993 | Shichman | |
| 5,203,864 A | 4/1993 | Phillips | |
| 5,217,471 A | 6/1993 | Burkhart | |
| 5,217,473 A | 6/1993 | Yoon | |
| 5,222,508 A | 6/1993 | Contarini | |
| 5,222,961 A | 6/1993 | Nakao et al. | |
| 5,222,963 A | 6/1993 | Brinkerhoff et al. | |
| 5,224,946 A | 7/1993 | Hayhurst et al. | |
| 5,234,430 A | 8/1993 | Huebner | |
| 5,234,445 A | 8/1993 | Walker et al. | |
| 5,250,053 A | 10/1993 | Snyder | |
| 5,251,611 A | 10/1993 | Zehel et al. | |
| 5,254,126 A | 10/1993 | Filipi et al. | |
| 5,258,016 A | 11/1993 | Dipoto et al. | |
| 5,261,916 A | 11/1993 | Engelson | |
| 5,268,001 A | 12/1993 | Nicholson et al. | |
| 5,282,827 A | 2/1994 | Kensey et al. | |
| 5,284,488 A | 2/1994 | Sideris | |
| 5,289,817 A | 3/1994 | Williams et al. | |
| 5,300,065 A | 4/1994 | Anderson | |
| 5,304,184 A | 4/1994 | Hathaway et al. | |
| 5,304,195 A | 4/1994 | Twyford et al. | |
| 5,304,204 A | 4/1994 | Bregen | |
| 5,316,543 A | 5/1994 | Eberbach | |
| 5,327,914 A | 7/1994 | Shlain | |
| 5,330,503 A | 7/1994 | Yoon | |
| 5,334,217 A | 8/1994 | Das | |
| 5,336,222 A | 8/1994 | Durgin et al. | |
| 5,336,227 A | 8/1994 | Nakao et al. | |
| 5,337,732 A | 8/1994 | Grundfest et al. | |
| 5,337,733 A | 8/1994 | Bauerfeind et al. | |
| 5,342,376 A | 8/1994 | Ruff | |
| 5,345,949 A | 9/1994 | Shlain | |
| 5,348,259 A | 9/1994 | Blanco et al. | |
| 5,350,399 A | 9/1994 | Erlebacher et al. | |
| 5,354,298 A | 10/1994 | Lee et al. | |
| 5,366,459 A | 11/1994 | Yoon | |
| 5,366,479 A | 11/1994 | Mcgarry et al. | |
| 5,372,146 A | 12/1994 | Branch | |
| 5,372,604 A | 12/1994 | Trott | |
| 5,374,275 A | 12/1994 | Bradley et al. | |
| 5,380,334 A | 1/1995 | Torrie et al. | |
| 5,382,231 A | 1/1995 | Shlain | |
| 5,395,030 A | 3/1995 | Kuramoto et al. | |
| 5,395,331 A * | 3/1995 | O'Neill et al. | 606/194 |
| 5,403,326 A | 4/1995 | Harrison et al. | |
| 5,403,329 A | 4/1995 | Hinchcliffe | |
| 5,417,691 A | 5/1995 | Hayhurst | |
| 5,417,699 A | 5/1995 | Klein et al. | |
| 5,425,744 A | 6/1995 | Fagan et al. | |
| 5,429,583 A | 7/1995 | Paulus et al. | |
| 5,429,598 A | 7/1995 | Waxman et al. | |
| 5,431,666 A | 7/1995 | Sauer et al. | |
| 5,433,721 A | 7/1995 | Hooven et al. | |
| 5,433,727 A | 7/1995 | Sideris | |
| 5,437,266 A | 8/1995 | Mcpherson et al. | |
| 5,437,680 A | 8/1995 | Yoon | |
| 5,437,681 A | 8/1995 | Meade et al. | |
| 5,445,167 A | 8/1995 | Yoon et al. | |
| 5,458,609 A | 10/1995 | Gordon et al. | |
| 5,462,560 A | 10/1995 | Stevens | |
| 5,462,561 A | 10/1995 | Voda | |
| 5,465,894 A | 11/1995 | Clark et al. | |
| 5,470,337 A | 11/1995 | Moss | |
| 5,470,338 A | 11/1995 | Whitfield et al. | |
| 5,476,470 A | 12/1995 | Fitzgibbons | |
| 5,478,354 A | 12/1995 | Tovey et al. | |
| 5,480,405 A | 1/1996 | Yoon | |
| 5,496,332 A | 3/1996 | Sierra et al. | |
| 5,496,334 A | 3/1996 | Klundt et al. | |
| 5,499,991 A | 3/1996 | Garman et al. | |
| 5,501,691 A | 3/1996 | Goldrath | |
| 5,507,811 A | 4/1996 | Koike et al. | |
| 5,520,691 A | 5/1996 | Branch | |
| 5,520,701 A | 5/1996 | Lerch | |
| 5,522,843 A | 6/1996 | Zang | |
| 5,527,321 A | 6/1996 | Hinchliffe | |
| 5,527,322 A | 6/1996 | Klein et al. | |
| 5,527,342 A | 6/1996 | Pietrzak et al. | |
| 5,531,759 A | 7/1996 | Kensey et al. | |
| 5,531,788 A | 7/1996 | Dibie et al. | |
| 5,535,759 A | 7/1996 | Wilk | |
| 5,540,704 A | 7/1996 | Gordon et al. | |
| 5,549,621 A | 8/1996 | Bessler et al. | |
| 5,556,410 A | 9/1996 | Mittermeir et al. | |
| 5,558,665 A | 9/1996 | Kieturakis | |
| 5,562,684 A | 10/1996 | Kammerer | |
| 5,562,686 A | 10/1996 | Sauer et al. | |
| 5,562,688 A | 10/1996 | Riza | |
| 5,569,274 A | 10/1996 | Rapacki et al. | |
| 5,569,306 A | 10/1996 | Thal | |
| 5,571,116 A | 11/1996 | Bolanos et al. | |
| 5,571,119 A | 11/1996 | Atala | |
| 5,573,496 A | 11/1996 | Mcpherson et al. | |
| 5,573,540 A | 11/1996 | Yoon | |
| 5,573,548 A | 11/1996 | Nazre et al. | |
| 5,578,045 A | 11/1996 | Das | |
| 5,582,616 A | 12/1996 | Bolduc et al. | |

| Patent | Date | Name | | Patent | Date | Name |
|---|---|---|---|---|---|---|
| 5,584,835 A | 12/1996 | Greenfield | | 5,891,168 A | 4/1999 | Thal |
| 5,584,859 A | 12/1996 | Brotz | | 5,893,856 A | 4/1999 | Jacob et al. |
| 5,601,557 A | 2/1997 | Hayhurst | | 5,895,404 A | 4/1999 | Ruiz |
| 5,603,718 A | 2/1997 | Xu | | 5,897,417 A | 4/1999 | Grey |
| 5,613,974 A | 3/1997 | Andreas et al. | | 5,897,562 A | 4/1999 | Bolanos et al. |
| 5,613,975 A | 3/1997 | Christy | | 5,899,920 A | 5/1999 | Desatnick et al. |
| 5,624,381 A | 4/1997 | Kieturakis | | 5,899,921 A | 5/1999 | Caspari et al. |
| 5,626,553 A * | 5/1997 | Frassica et al. ............... 600/146 | | 5,901,895 A | 5/1999 | Heaton et al. |
| 5,626,588 A | 5/1997 | Sauer et al. | | 5,902,254 A | 5/1999 | Magram |
| 5,626,614 A | 5/1997 | Hart | | 5,904,647 A * | 5/1999 | Ouchi ........................... 600/104 |
| 5,630,540 A | 5/1997 | Blewett | | 5,916,147 A | 6/1999 | Boury |
| 5,632,752 A | 5/1997 | Buelna | | 5,916,224 A | 6/1999 | Esplin |
| 5,643,274 A | 7/1997 | Sander et al. | | 5,921,915 A | 7/1999 | Aznoian et al. |
| 5,643,295 A | 7/1997 | Yoon | | 5,925,059 A | 7/1999 | Palermo et al. |
| 5,643,317 A | 7/1997 | Pavcnik et al. | | 5,928,264 A | 7/1999 | Sugarbaker et al. |
| 5,643,320 A | 7/1997 | Lower et al. | | 5,944,738 A | 8/1999 | Amplatz et al. |
| 5,651,788 A | 7/1997 | Fleischer et al. | | 5,947,983 A | 9/1999 | Solar et al. |
| 5,658,312 A | 8/1997 | Green et al. | | 5,947,997 A | 9/1999 | Pavcnik et al. |
| 5,658,313 A | 8/1997 | Thal | | 5,948,001 A | 9/1999 | Larsen |
| 5,662,587 A | 9/1997 | Grundfest et al. | | 5,954,732 A | 9/1999 | Hart et al. |
| 5,662,662 A | 9/1997 | Bishop et al. | | 5,961,440 A | 10/1999 | Schweich et al. |
| 5,662,663 A | 9/1997 | Shallman | | 5,964,765 A | 10/1999 | Fenton et al. |
| 5,665,109 A | 9/1997 | Yoon | | 5,964,782 A | 10/1999 | Lafontaine et al. |
| 5,665,112 A | 9/1997 | Thal | | 5,964,783 A | 10/1999 | Grafton et al. |
| 5,667,513 A | 9/1997 | Torrie et al. | | 5,976,073 A | 11/1999 | Ouchi |
| 5,669,917 A | 9/1997 | Sauer et al. | | 5,976,127 A | 11/1999 | Lax |
| 5,676,674 A | 10/1997 | Bolanos et al. | | 5,976,158 A | 11/1999 | Adams et al. |
| 5,679,005 A | 10/1997 | Einstein | | 5,976,159 A | 11/1999 | Bolduc et al. |
| 5,683,417 A | 11/1997 | Cooper | | 5,980,558 A | 11/1999 | Wiley |
| 5,683,419 A | 11/1997 | Thal | | 5,984,933 A | 11/1999 | Yoon |
| 5,690,655 A | 11/1997 | Hart et al. | | 5,993,476 A | 11/1999 | Groiso |
| 5,693,060 A | 12/1997 | Martin | | 6,013,083 A | 1/2000 | Bennett |
| 5,700,273 A | 12/1997 | Buelna et al. | | 6,027,523 A | 2/2000 | Schmieding |
| 5,702,421 A | 12/1997 | Schneidt | | 6,033,430 A | 3/2000 | Bonutti |
| 5,707,394 A | 1/1998 | Miller et al. | | 6,036,699 A | 3/2000 | Andreas et al. |
| 5,709,708 A | 1/1998 | Thal | | 6,042,155 A | 3/2000 | Lockwood |
| 5,713,903 A | 2/1998 | Sander et al. | | 6,045,497 A | 4/2000 | Schweich et al. |
| 5,720,765 A | 2/1998 | Thal | | 6,045,573 A | 4/2000 | Wenstrom et al. |
| 5,724,978 A | 3/1998 | Tenhoff | | 6,050,936 A | 4/2000 | Schweich et al. |
| 5,725,552 A | 3/1998 | Kotula et al. | | 6,053,935 A | 4/2000 | Brenneman et al. |
| 5,728,045 A * | 3/1998 | Komi ............................ 600/156 | | 6,059,715 A | 5/2000 | Schweich et al. |
| 5,732,707 A | 3/1998 | Widder et al. | | 6,059,719 A | 5/2000 | Yamamoto et al. |
| 5,741,297 A | 4/1998 | Simon | | 6,074,401 A | 6/2000 | Gardiner et al. |
| 5,749,828 A | 5/1998 | Solomon et al. | | 6,077,214 A | 6/2000 | Mortier et al. |
| 5,749,893 A | 5/1998 | Vidal et al. | | 6,077,281 A | 6/2000 | Das |
| 5,752,963 A | 5/1998 | Allard et al. | | 6,077,291 A | 6/2000 | Das |
| 5,759,151 A | 6/1998 | Sturges | | 6,079,414 A | 6/2000 | Roth |
| 5,766,189 A | 6/1998 | Matsuno | | 6,086,600 A | 7/2000 | Kortenbach |
| 5,779,719 A | 7/1998 | Klein et al. | | 6,110,183 A | 8/2000 | Cope |
| 5,782,859 A | 7/1998 | Nicholas et al. | | 6,113,609 A | 9/2000 | Adams |
| 5,782,865 A | 7/1998 | Grotz | | 6,113,611 A | 9/2000 | Allen et al. |
| 5,787,897 A | 8/1998 | Kieturakis | | 6,119,913 A | 9/2000 | Adams et al. |
| 5,792,152 A | 8/1998 | Klein et al. | | 6,149,658 A | 11/2000 | Gardiner et al. |
| 5,792,153 A | 8/1998 | Swain et al. | | 6,152,935 A | 11/2000 | Kammerer et al. |
| 5,797,929 A | 8/1998 | Andreas et al. | | 6,152,946 A | 11/2000 | Broome et al. |
| 5,797,960 A | 8/1998 | Stevens et al. | | 6,159,146 A | 12/2000 | El Gazayerli |
| 5,810,849 A | 9/1998 | Kontos | | 6,162,168 A | 12/2000 | Schweich et al. |
| 5,810,851 A | 9/1998 | Yoon | | 6,165,119 A | 12/2000 | Schweich et al. |
| 5,810,853 A | 9/1998 | Yoon | | 6,165,120 A | 12/2000 | Schweich et al. |
| 5,810,882 A | 9/1998 | Bolduc et al. | | 6,167,889 B1 | 1/2001 | Benetti |
| 5,814,070 A | 9/1998 | Borzone et al. | | 6,171,320 B1 | 1/2001 | Monassevitch |
| 5,817,110 A | 10/1998 | Kronner | | 6,174,323 B1 | 1/2001 | Biggs et al. |
| 5,823,956 A | 10/1998 | Roth et al. | | 6,179,195 B1 | 1/2001 | Adams et al. |
| 5,824,011 A | 10/1998 | Stone et al. | | 6,179,776 B1 | 1/2001 | Adams et al. |
| 5,827,298 A | 10/1998 | Hart et al. | | 6,183,411 B1 | 2/2001 | Mortier et al. |
| 5,829,447 A | 11/1998 | Stevens et al. | | RE37,117 E | 3/2001 | Palermo |
| 5,836,955 A | 11/1998 | Buelna et al. | | 6,197,022 B1 | 3/2001 | Baker |
| 5,840,078 A | 11/1998 | Yerys | | 6,214,007 B1 | 4/2001 | Anderson |
| 5,843,084 A | 12/1998 | Hart et al. | | 6,228,023 B1 | 5/2001 | Zaslavsky et al. |
| 5,843,126 A | 12/1998 | Jameel | | 6,231,561 B1 | 5/2001 | Frazier et al. |
| 5,846,261 A | 12/1998 | Kotula et al. | | 6,245,079 B1 | 6/2001 | Nobles et al. |
| 5,855,614 A | 1/1999 | Stevens et al. | | 6,260,552 B1 | 7/2001 | Mortier et al. |
| 5,860,991 A | 1/1999 | Klein et al. | | 6,261,222 B1 | 7/2001 | Schweich et al. |
| 5,861,003 A | 1/1999 | Latson et al. | | 6,264,602 B1 | 7/2001 | Mortier et al. |
| 5,865,791 A | 2/1999 | Whayne et al. | | 6,270,515 B1 | 8/2001 | Linden et al. |
| 5,868,762 A | 2/1999 | Cragg et al. | | 6,283,973 B1 | 9/2001 | Hubbard et al. |
| 5,879,371 A | 3/1999 | Gardiner et al. | | 6,290,674 B1 | 9/2001 | Roue et al. |
| 5,887,594 A | 3/1999 | LoCicero, III | | 6,293,907 B1 * | 9/2001 | Axon et al. .................... 600/114 |
| 5,888,247 A | 3/1999 | Benetti | | 6,293,956 B1 | 9/2001 | Crainich et al. |

| | | | | | | |
|---|---|---|---|---|---|---|
| 6,296,656 | B1 | 10/2001 | Bolduc et al. | 2002/0078967 A1 | 6/2002 | Sixto, Jr. et al. |
| 6,306,159 | B1 | 10/2001 | Schwartz et al. | 2002/0082621 A1 | 6/2002 | Schurr et al. |
| 6,312,437 | B1 | 11/2001 | Kortenbach | 2002/0082622 A1 | 6/2002 | Kane |
| 6,315,789 | B1 | 11/2001 | Cragg | 2002/0107530 A1 | 8/2002 | Sauer et al. |
| 6,322,563 | B1 | 11/2001 | Cummings et al. | 2002/0120178 A1 | 8/2002 | Tartaglia et al. |
| 6,322,580 | B1 | 11/2001 | Kanner | 2002/0147385 A1 | 10/2002 | Butler et al. |
| 6,332,468 | B1 | 12/2001 | Benetti | 2002/0161281 A1 | 10/2002 | Jaffe et al. |
| 6,332,863 | B1 | 12/2001 | Schweich et al. | 2002/0183768 A1 | 12/2002 | Deem et al. |
| 6,332,864 | B1 | 12/2001 | Schweich et al. | 2002/0193661 A1 | 12/2002 | Belson |
| 6,332,893 | B1 | 12/2001 | Mortier et al. | 2002/0193662 A1 | 12/2002 | Belson |
| 6,336,940 | B1 | 1/2002 | Graf et al. | 2002/0193816 A1 | 12/2002 | Laufer et al. |
| 6,346,074 | B1 | 2/2002 | Roth | 2003/0009085 A1 | 1/2003 | Arai et al. |
| 6,348,064 | B1 | 2/2002 | Kanner | 2003/0045778 A1 | 3/2003 | Ohline et al. |
| 6,352,503 | B1 * | 3/2002 | Matsui et al. ................ 600/104 | 2003/0055442 A1 | 3/2003 | Laufer et al. |
| 6,355,052 | B1 | 3/2002 | Neuss et al. | 2003/0065359 A1 | 4/2003 | Weller et al. |
| 6,358,197 | B1 | 3/2002 | Silverman et al. | 2003/0109892 A1 | 6/2003 | Deem et al. |
| 6,363,938 | B2 | 4/2002 | Saadat et al. | 2003/0120265 A1 | 6/2003 | Deem et al. |
| 6,368,339 | B1 | 4/2002 | Amplatz | 2003/0139752 A1 | 7/2003 | Pasricha et al. |
| 6,387,104 | B1 | 5/2002 | Pugsley, Jr. | 2003/0158582 A1 | 8/2003 | Bonutti et al. |
| 6,394,949 | B1 | 5/2002 | Crowley et al. | 2003/0167062 A1 | 9/2003 | Gambale et al. |
| 6,402,679 | B1 | 6/2002 | Mortier et al. | 2003/0171651 A1 | 9/2003 | Page et al. |
| 6,402,680 | B2 | 6/2002 | Mortier et al. | 2003/0171760 A1 | 9/2003 | Gambale |
| 6,406,420 | B1 | 6/2002 | Mccarthy et al. | 2003/0176890 A1 | 9/2003 | Buckman et al. |
| H2037 | H | 7/2002 | Yates et al. | 2003/0181924 A1 | 9/2003 | Yamamoto et al. |
| 6,423,087 | B1 | 7/2002 | Sawada | 2003/0204205 A1 | 10/2003 | Sauer et al. |
| 6,425,911 | B1 | 7/2002 | Akerfeldt et al. | 2003/0208209 A1 | 11/2003 | Gambale et al. |
| 6,447,533 | B1 | 9/2002 | Adams | 2003/0216613 A1 | 11/2003 | Suzuki et al. |
| 6,494,888 | B1 | 12/2002 | Laufer et al. | 2003/0225312 A1 | 12/2003 | Suzuki et al. |
| 6,506,196 | B1 | 1/2003 | Laufer | 2003/0229296 A1 | 12/2003 | Ishikawa et al. |
| 6,533,796 | B1 | 3/2003 | Sauer et al. | 2003/0233066 A1 | 12/2003 | Ewers et al. |
| 6,537,285 | B1 | 3/2003 | Hatasaka, Jr. et al. | 2003/0236505 A1 | 12/2003 | Bonadio et al. |
| 6,540,789 | B1 | 4/2003 | Silverman et al. | 2003/0236536 A1 | 12/2003 | Grigoryants et al. |
| 6,551,315 | B2 | 4/2003 | Kortenbach et al. | 2003/0236549 A1 | 12/2003 | Bonadio et al. |
| 6,554,780 | B1 | 4/2003 | Sampson et al. | 2004/0010271 A1 | 1/2004 | Kortenbach |
| 6,554,793 | B1 | 4/2003 | Pauker et al. | 2004/0030347 A1 | 2/2004 | Gannoe et al. |
| 6,554,845 | B1 | 4/2003 | Fleenor et al. | 2004/0034371 A1 | 2/2004 | Lehman et al. |
| 6,558,400 | B2 | 5/2003 | Deem et al. | 2004/0049095 A1 | 3/2004 | Goto et al. |
| 6,572,629 | B2 | 6/2003 | Kalloo et al. | 2004/0059346 A1 | 3/2004 | Adams et al. |
| 6,610,056 | B2 | 8/2003 | Durgin et al. | 2004/0082963 A1 | 4/2004 | Gannoe et al. |
| 6,641,592 | B1 | 11/2003 | Sauer et al. | 2004/0088008 A1 | 5/2004 | Gannoe et al. |
| 6,656,194 | B1 | 12/2003 | Gannoe et al. | 2004/0092974 A1 | 5/2004 | Gannoe et al. |
| 6,663,639 | B1 | 12/2003 | Laufer et al. | 2004/0093091 A1 | 5/2004 | Gannoe et al. |
| 6,695,764 | B2 | 2/2004 | Silverman et al. | 2004/0122452 A1 | 6/2004 | Deem et al. |
| 6,695,866 | B1 * | 2/2004 | Kuehn et al. ................ 606/213 | 2004/0122453 A1 | 6/2004 | Deem et al. |
| 6,716,232 | B1 | 4/2004 | Vidal et al. | 2004/0122456 A1 | 6/2004 | Saadat et al. |
| 6,719,763 | B2 | 4/2004 | Chung et al. | 2004/0122474 A1 | 6/2004 | Gellman et al. |
| 6,719,764 | B1 | 4/2004 | Gellman et al. | 2004/0138682 A1 | 7/2004 | Onuki et al. |
| 6,736,828 | B1 | 5/2004 | Adams et al. | 2004/0147941 A1 | 7/2004 | Takemoto |
| 6,746,460 | B2 | 6/2004 | Gannoe et al. | 2004/0162568 A1 | 8/2004 | Saadat et al. |
| 6,755,843 | B2 | 6/2004 | Chung et al. | 2004/0176784 A1 | 9/2004 | Okada |
| 6,761,685 | B2 | 7/2004 | Adams et al. | 2004/0193117 A1 | 9/2004 | Laufer et al. |
| 6,767,339 | B2 * | 7/2004 | Reydel ................ 604/264 | 2004/0193184 A1 | 9/2004 | Laufer et al. |
| 6,773,440 | B2 | 8/2004 | Gannoe et al. | 2004/0193193 A1 | 9/2004 | Laufer et al. |
| 6,773,441 | B1 | 8/2004 | Laufer et al. | 2004/0193194 A1 | 9/2004 | Laufer et al. |
| 6,821,285 | B2 | 11/2004 | Laufer et al. | 2004/0194790 A1 | 10/2004 | Laufer et al. |
| 6,835,199 | B2 | 12/2004 | McGuckin, Jr. et al. | 2004/0210243 A1 | 10/2004 | Gannoe et al. |
| 7,431,725 | B2 | 10/2008 | Stack et al. | 2004/0215180 A1 | 10/2004 | Starkebaum et al. |
| 2001/0000040 | A1 | 3/2001 | Adams et al. | 2004/0215216 A1 | 10/2004 | Gannoe et al. |
| 2001/0016675 | A1 | 8/2001 | Mortier et al. | 2004/0225305 A1 | 11/2004 | Ewers et al. |
| 2001/0025171 | A1 | 9/2001 | Mortier et al. | 2004/0243152 A1 | 12/2004 | Taylor et al. |
| 2001/0049509 | A1 | 12/2001 | Sekine et al. | 2004/0249362 A1 | 12/2004 | Levine et al. |
| 2001/0051815 | A1 | 12/2001 | Esplin | 2004/0249392 A1 | 12/2004 | Mikkaichi et al. |
| 2001/0056282 | A1 | 12/2001 | Sonnenschein et al. | 2004/0249395 A1 | 12/2004 | Mikkaichi et al. |
| 2002/0010490 | A1 | 1/2002 | Schaller et al. | 2005/0033320 A1 | 2/2005 | Mcguckin et al. |
| 2002/0013608 | A1 | 1/2002 | Elattrache et al. | 2005/0033328 A1 | 2/2005 | Laufer et al. |
| 2002/0019649 | A1 | 2/2002 | Sikora et al. | 2005/0043758 A1 | 2/2005 | Golden et al. |
| 2002/0022851 | A1 | 2/2002 | Kalloo et al. | 2005/0049617 A1 | 3/2005 | Chatlynne et al. |
| 2002/0029080 | A1 | 3/2002 | Mortier et al. | 2005/0070931 A1 | 3/2005 | Li et al. |
| 2002/0040226 | A1 | 4/2002 | Laufer et al. | 2005/0080444 A1 | 4/2005 | Kraemer et al. |
| 2002/0055757 | A1 | 5/2002 | Torre et al. | 2005/0096750 A1 | 5/2005 | Kagan et al. |
| 2002/0058855 | A1 | 5/2002 | Schweich et al. | 2005/0203489 A1 | 9/2005 | Saadat et al. |
| 2002/0058905 | A1 | 5/2002 | Madrid et al. | 2005/0216040 A1 | 9/2005 | Gertner et al. |
| 2002/0062062 | A1 | 5/2002 | Belson et al. | 2005/0216042 A1 | 9/2005 | Gertner |
| 2002/0065534 | A1 | 5/2002 | Hermann et al. | 2006/0020276 A1 | 1/2006 | Saadat et al. |
| 2002/0068849 | A1 | 6/2002 | Schweich et al. | | | |
| 2002/0068945 | A1 | 6/2002 | Sixto, Jr. et al. | | | |
| 2002/0072761 | A1 | 6/2002 | Abrams et al. | FR | 2 768 324 A1 | 3/1999 |
| 2002/0077524 | A1 | 6/2002 | Schweich et al. | GB | 2 165 559 A | 4/1986 |
| 2002/0077661 | A1 | 6/2002 | Saadat | WO | WO 92/04870 A1 | 4/1992 |

FOREIGN PATENT DOCUMENTS

| | | |
|---|---|---|
| WO | WO 95/25468 A1 | 9/1995 |
| WO | WO 99/22649 A2 | 5/1999 |
| WO | WO 00/78227 A1 | 12/2000 |
| WO | WO 00/78229 A1 | 12/2000 |
| WO | WO 01/66018 A1 | 9/2001 |
| WO | WO 01/85034 A1 | 11/2001 |
| WO | WO 01/87144 A1 | 11/2001 |
| WO | WO 01/89370 A2 | 11/2001 |
| WO | WO 01/89393 A1 | 11/2001 |
| WO | WO 02/24080 A2 | 3/2002 |
| WO | WO 02/39880 A2 | 5/2002 |
| WO | WO 02/094105 A2 | 11/2002 |
| WO | WO 03/007796 A2 | 1/2003 |
| WO | WO 03/090633 A2 | 11/2003 |
| WO | WO 03/092509 A1 | 11/2003 |
| WO | WO 03/096909 A1 | 11/2003 |
| WO | WO 03/099137 A2 | 12/2003 |
| WO | WO 03/105732 A1 | 12/2003 |
| WO | WO 2004/004544 A2 | 1/2004 |
| WO | WO 2004/019787 A2 | 3/2004 |
| WO | WO 2004/019788 A2 | 3/2004 |
| WO | WO 2004/021865 A2 | 3/2004 |
| WO | WO 2004/021867 A2 | 3/2004 |
| WO | WO 2004/021868 A2 | 3/2004 |
| WO | WO 2004/021873 A2 | 3/2004 |
| WO | WO 2004/021894 A1 | 3/2004 |
| WO | WO 2004/084808 A2 | 10/2004 |
| WO | WO 2004/103189 A1 | 12/2004 |
| WO | WO 2005/037072 A2 | 4/2005 |
| WO | WO 2005/037152 A1 | 4/2005 |

OTHER PUBLICATIONS

Brolin et al., "Experimental Evaluation of Techniques of Gastric Paritioning for Morbid Obesity," *Surgery, Gynecology & Obstetrics*, vol. 153, (Dec. 1981), pp. 878-882.

Johnston et al. "The Magenstrasse and Mill Operation of Morbid Obesity", *Obesity Surgery* 13, (2003), pp. 10-16.

Okudaira et al., "The Healing and Tensile Strength of the Gastroplasty Staple Line," *The American Surgeon*, Oct. 1984, pp. 564-568.

Chuttani et al., "A Novel Endoscopic Full-thickness Plicator for Treatment of GERD: An Animal Model Study, " *Gastrointestinal Endoscopy*, vol. 26, No. 1,(2002), pp. 116-122.

Mason, "Development of Future of Gastroplasties for Morbid Obesity," *Arch Surg*, vol. 138 (Apr. 2003), pp. 362-366.

AngioLINK: The Expanding Vascular Staple [brochure], 1 page total, Nov. 2004.

Spivak, et al. "Endoluminal Surgery" *Surgical Endoscopy*, 11:321-325, 1997.

Surgical Dynamics, Inc,. The S D sorb Meniscai Stapler [brochure], 3 pages total, 1997.

Sutura, The Next Generation in Vascular Suturing Devices: Superstitch [brochure] 2 pages total, Sep. 2004.

Suzuki, et al, "Development of an Endoscopic Robotic System with Two hands for 518 Various Gastric Tube Surgeries", *Stud Health Technol Inform*, 94:349-53 (Abstract Only), 2003.

File History for U.S. Appl. No. 10/797,910 filed Mar. 9, 2004 in the name of Michlitsch et al.

File History for U.S. Appl. No. 10/841,233 filed May 7, 2004 in the name of Swanstrom et al.

File History for U.S. Appl. No. 10/954,658 filed Sep. 29, 2004 in the name of Saadat et al.

File History for U.S. Appl. No. 11/069,890 filed Feb. 28, 2005 in the name of Saadat et al.

File History for U.S. Appl. No. 12/426,894 filed Apr. 20, 2009 in the name of Swanstrom et al.

* cited by examiner

METHODS AND APPARATUS FOR PERFORMING ENDOLUMINAL GASTROPLASTY

FIELD OF INVENTION

The present invention relates to methods and apparatus for endoluminally partitioning a patient's stomach to restrict the passage of food therethrough.

BACKGROUND OF THE INVENTION

Extreme or morbid obesity is a serious medical condition pervasive in the United States and other countries. Its complications include hypertension, diabetes, coronary artery disease, stroke, congestive heart failure, multiple orthopaedic problems and pulmonary insufficiency with markedly decreased life expectancy.

Several surgical techniques have been developed to treat morbid obesity, including bypassing an absorptive surface of the small intestine, bypassing a portion of the stomach, and reducing or partitioning the stomach size, e.g., via Vertical Banded Gastroplasty ("VBG") or Magenstrasse and Mill. These procedures may be difficult to perform in morbidly obese patients and/or may present numerous potentially life-threatening post-operative complications. Thus, less invasive techniques have been pursued.

U.S. Pat. Nos. 4,416,267 and 4,485,805 to Garren et al. and Foster, Jr., respectively, propose disposal of an inflated bag within a patient's stomach to decrease the effective volume of the stomach that is available to store food. Accordingly, the patient is satiated without having to consume a large amount of food. A common problem with these inflated bags is that, since the bags float freely within the patient's stomach, the bags may migrate to, and block, a patient's pyloric opening, the portal leading from the stomach to the duodenum, thereby restricting passage of food to the remainder of the gastrointestinal tract.

Apparatus and methods also are known in which an adjustable elongated gastric band is laparoscopically disposed around the outside of a patient's stomach near the esophagus to form a collar that, when tightened, squeezes the stomach into an hourglass shape, thereby providing a stoma that limits the amount of food that a patient may consume comfortably. An example of an adjustable gastric band is the LAP-BAND® made by INAMED Health of Santa Barbara, Calif.

Numerous disadvantages are associated with using an adjustable gastric band. First, the band may be dislodged if the patient grossly overeats, thereby requiring additional invasive surgery to either reposition or remove the band. Similarly, overeating may cause the band to injure the stomach wall if the stomach over-expands. Laparoscopic disposal of the gastric band around the stomach requires a complex procedure, requires considerable skill on the part of the clinician, and is not free of dangerous complications.

In view of the drawbacks associated with prior art techniques for treating morbid obesity, it would be desirable to provide methods and apparatus for endoluminally performing gastroplasty.

BRIEF SUMMARY OF THE INVENTION

Endoluminal gastroplasty is achieved by providing methods and apparatus for endoluminally partitioning a patient's stomach to restrict the passage of food therethrough. In one variation, the apparatus comprises a sizing tube (e.g., a modified bougie) and a steerable guide that may be advanced and/or retracted within the sizing tube. Endoluminal instruments or tools may be advanced along or through the steerable guide, or may be coupled thereto.

The sizing tube preferably comprises reversible adhering elements, such as suction ports, hooks or barbs, disposed along a length thereof for adhering the tube along the lesser curvature of a patient's stomach. The tube preferably also comprises a lumen in which the steerable guide may be reversibly disposed, and at least one side port or slot along the length of the tube, from which the steerable guide may exit the tube lumen. Furthermore, the sizing tube may comprise an optional inflatable member disposed near or at a distal region of the tube for distally securing the tube to the patient's pylorus in a reversible manner.

Applicant has previously described exemplary steerable guides, for example, in co-pending U.S. patent application Ser. No. 10/797,485, filed Mar. 9, 2004, which is incorporated herein by reference in its entirety. That reference describes guides, or endoluminal tool deployment systems, having multiple lumens and/or sections. Different sections of the guides may have varying capacities for steering, shape-locking or rigidizing, retroflexing, etc.

Applicant also has previously described exemplary instruments or tools configured for coupling to, or advancement through/along, a steerable guide, for example, in Applicant's co-pending U.S. patent application Ser. No. 10/735,030, filed Dec. 12, 2003, which is incorporated herein by reference in its entirety. Such tools may include, but are not limited to, tools for endoluminally visualizing, grasping, plicating, manipulating, affixing and/or securing gastric tissue.

In one method of utilizing the apparatus, a pouch is endoluminally formed within a patient's stomach, thereby partitioning or reducing the stomach and restricting the flow of food therethrough. The pouch may form a Vertical Banded Gastroplasty or Magenstrasse and Mill in an endoluminal fashion. Advantageously, the sizing tube described previously may be used to properly size the pouch.

The method may comprise disposing the steerable guide within the lumen of the sizing tube and advancing the sizing tube down a patient's esophagus into the patient's stomach. The steerable guide may then be used to steer the sizing tube into a position whereby the length of the tube is disposed in proximity to the lesser curvature of the patient's stomach. The tube's distal region preferably is disposed in proximity to the patient's pylorus. The sizing tube's reversible adhering elements may be actuated to reversibly secure or couple the tube along its length to the lesser curvature of the patient's stomach. Likewise, the tube's optional inflatable member may be inflated to secure or couple the distal region of the tube against the patient's pylorus.

Next, the steerable guide may be retracted relative to the sizing tube, and may be steered such that it exits the lumen of the sizing tube at the tube's side port or slot. The guide may then be steered, shape-locked or rigidized, retroflexed, etc., to properly position tools deployed via the guide for formation of the endoluminal pouch. Illustrative methods of forming such a pouch with tools deployed from a steerable guide are described, for example, in Applicant's co-pending U.S. patent application Ser. No. 10/735,030, filed Dec. 12, 2003, which has been incorporated herein by reference. Advantageously, the endoluminal pouch may be formed about the sizing tube to ensure proper sizing of the pouch. Sizing tubes of various diameters may accordingly be utilized, provided that sufficient space is provided within the sizing tube for advancement of the appropriate tools. Thus, specified sizing tubes having a size which displaces a desired volume within the stomach may be utilized depending upon the desired size and volume of an endoluminal pouch to be formed about the sizing tube.

After formation of the pouch, the steerable guide and any instruments or tools may be retracted proximally within the lumen of the sizing tube for removal from the patient. Final formation of the pouch, e.g., via tightening of pre-placed sutures or anchors, optionally may be achieved after the steerable guide has been returned to the lumen of the sizing tube. At any time during or after formation of the pouch, the inflatable member of the sizing tube may be deflated, and its reversible adhering elements may be decoupled from the patient's stomach, pylorus, or duodenal tissue, depending upon where the sizing tube has been anchored, thereby facilitating removal of the sizing tube, as well as the steerable guide and any instruments, from the patient.

In a variation of the apparatus and method, the steerable guide may be provided with reversible adhering elements along at least a portion of its length. In such a configuration, no separate sizing tube may be required. Rather, the steerable guide may be reversibly coupled to, e.g., the lesser curvature of the patient's stomach, along a more proximal portion of its length disposed within the stomach. This more proximal portion may be used to properly size the endoluminal pouch. A more distal portion of the guide may be steered to facilitate formation of the pouch about the more proximal portion of the guide, with the more proximal portion facilitating proper sizing of the pouch.

Additional variations will be apparent to those of skill in the art.

DETAILED DESCRIPTION OF THE INVENTION

Figure 1A:
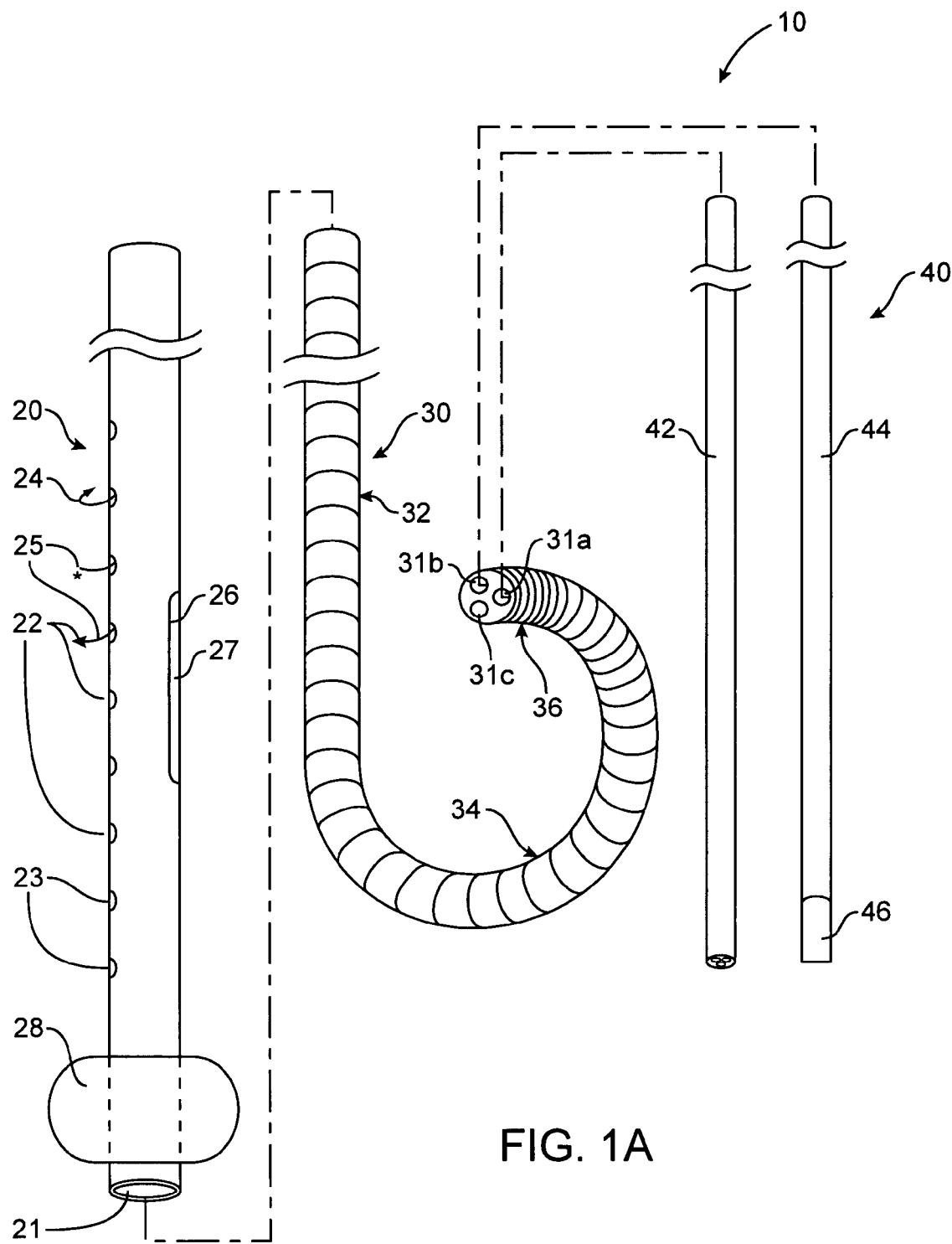
FIGS. 1A-1F are a schematic side view of one variation of the apparatus, detail perspective views of variations of a sizing tube of the apparatus, and a detail side view of a variation of the sizing tube.

Methods and apparatus for endoluminally partitioning a patient's stomach to restrict the passage of food therethrough are described.

With reference to FIG. 1, one variation of the apparatus is described. As seen in FIG. 1A, apparatus 10 comprises sizing tube 20, as well as steerable guide 30 that may be advanced within the sizing tube. Endoluminal instruments or tools 40, such as endoscope 42 and exemplary tool 44, may be advanced along or through the steerable guide, or may be coupled thereto.

Sizing tube 20 illustratively comprises a modified bougie having at least one reversible adhering element and preferably a plurality of reversible adhering elements 22 disposed along a length thereof for reversibly adhering the tube onto a surface of tissue within the patient, for instance, the lesser curvature of a patient's stomach. Elements 22 may comprise any known reversible adhering element, including, for example, suction ports 23, extendable or retractable hooks 24, extendable or retractable barbs 25 and combinations thereof.

Figure 1B:
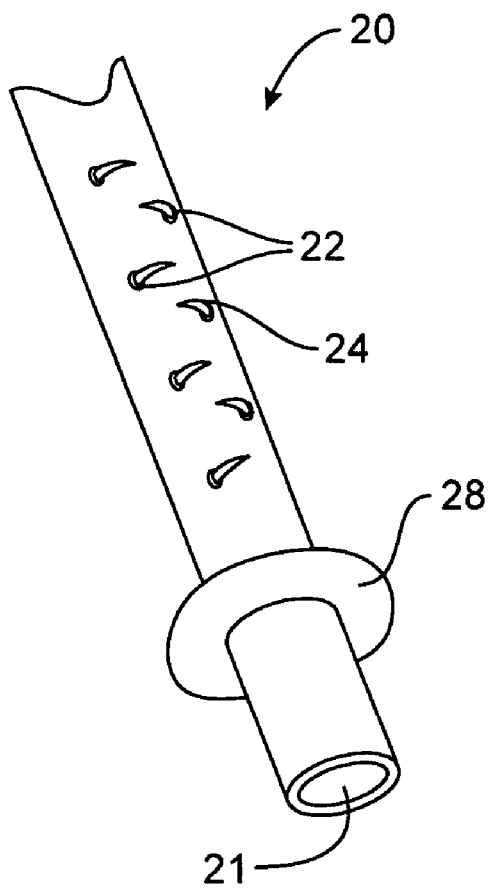
Figure 1C:
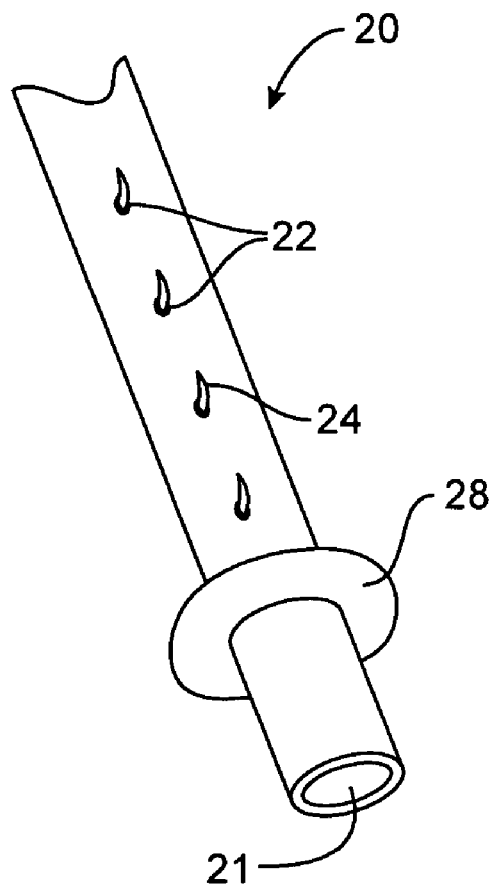
Figure 1D:
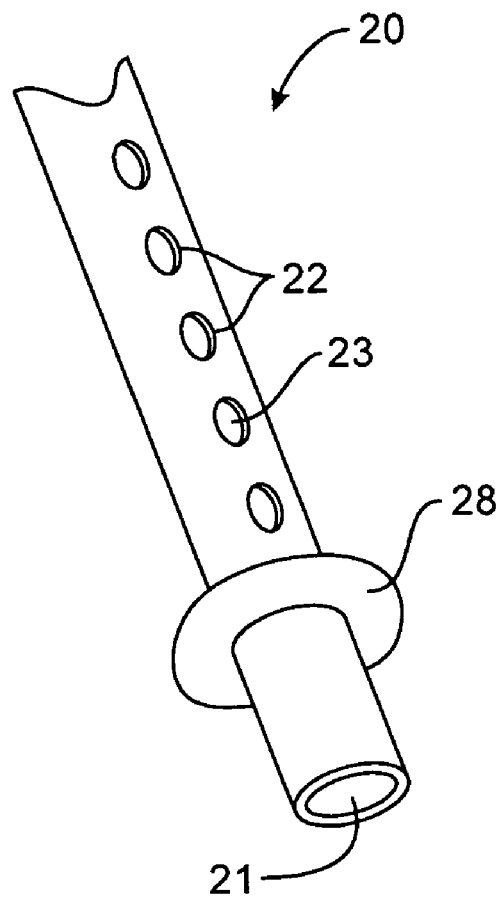
Figure 1E:
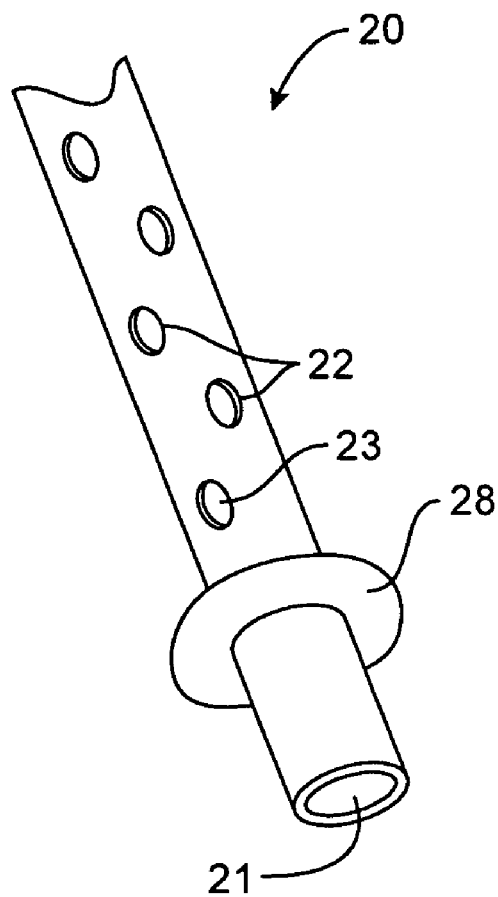
Figure 1F:
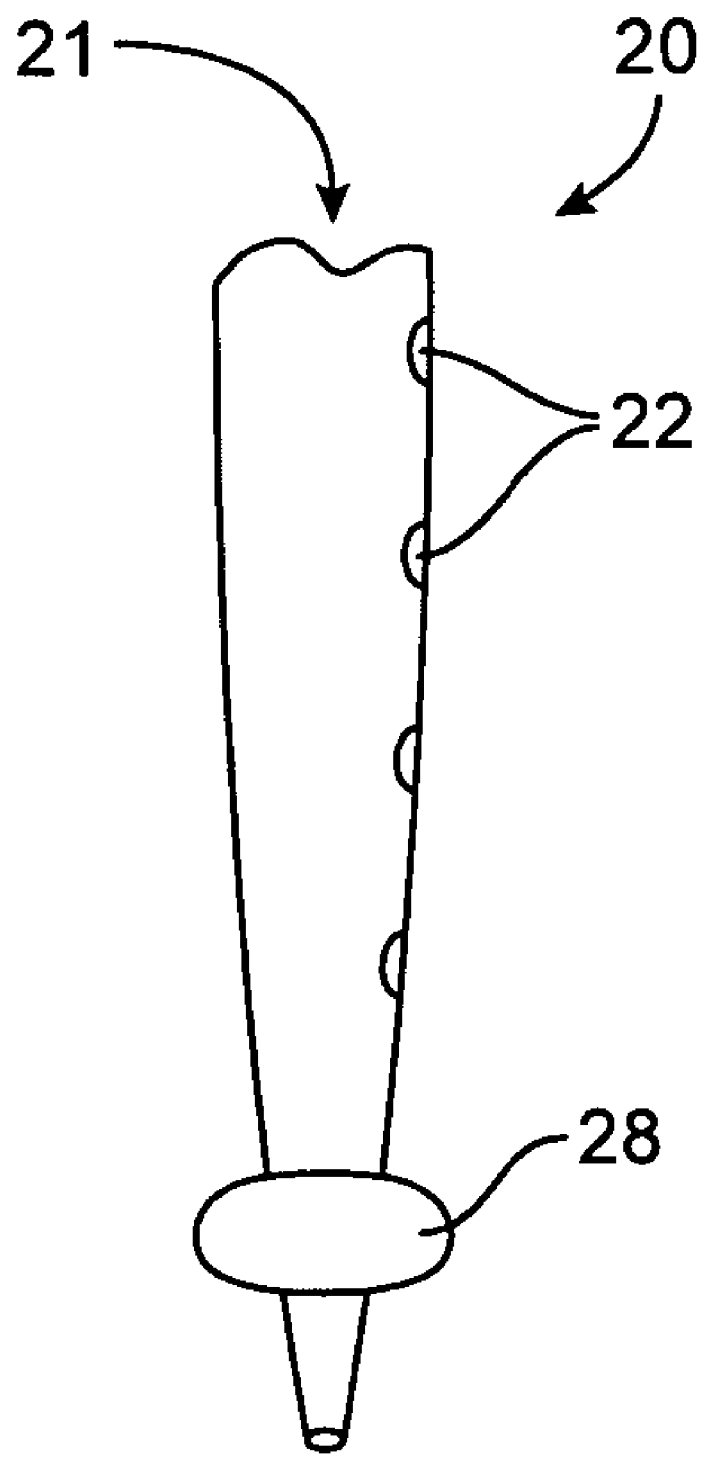

FIGS. 1B and 1C are detail perspective views of two exemplary variations of sizing tube 20 having different configurations of elements 22.

The reversibility of elements 22 may allow for sizing tube 20 to attach, at least temporarily, to the tissue surface without damaging the underlying tissue. Moreover, the ability for sizing tube 20 to adhere to the tissue may provide a relatively stable platform with respect to the surrounding tissue when advancing various tools therethrough. Additionally, if a plurality of elements 22 are utilized along the length of sizing tube 20, elements 22 may be collinearly aligned along the length at uniform distances relative to one another, as shown in the detail perspective view of FIG. 1D, or they may be positioned at various angles or staggered relative to one another, as shown in the detail perspective view of FIG. 1E.

As seen in FIG. 1A, sizing tube 20 also comprises lumen 21 in which steerable guide 30 may be advanced and retracted. Furthermore, sizing tube 20 may comprise one or more side ports or slots 26 that communicate with lumen 21 defined through sizing tube 20. Moreover, sizing tube 20 may be configured to have lumen 21 extend entirely through tube 20 or at least partially therethrough.

Slot 26 may be configured such that steerable guide 30 may exit lumen 21 via the slot. Optional seal 27, which may comprise a foam or rubber seal, may be provided to selectively close off slot 26. Sizing tube 20 optionally also may comprise inflatable member 28, e.g., a balloon, disposed near a distal region of the tube for distally securing the tube to, or distally of, the patient's pylorus, also in a reversible manner. An inflation lumen (not shown) may be provided for transferring an inflation fluid or gas to/from the inflatable member 28. Alternatively, rather than having an inflatable member 28 (or in addition to the inflatable member), other types of mechanical anchors which may or may not be retractable may be utilized, e.g., expandable baskets or cages, hooks, barbs, clamps, helical fasteners, etc.

Sizing tube 20 may have a maximum diameter, e.g., of less than or equal to about 40 Fr. Preferably, the sizing tube may have a maximum diameter of between about 26 Fr and 40 Fr, and more preferably a diameter between about 30 Fr and 36 Fr. Optionally, the diameter of tube 20 may vary along its length, e.g., in a tapered manner transitioning distally from a larger diameter to a smaller diameter along the length of tube 20, as shown in the side view of FIG. 1F.

Steerable guide 30 illustratively comprises multiple sections and multiple lumens. In FIG. 1A, although the guide illustratively comprises three lumens and three sections, it will be apparent to those of skill in the art that any alternative number of lumens and/or sections may be provided. Furthermore, the functionality of the sections may be altered or varied, as desired. Exemplary steerable guides are described, for example, in Applicant's co-pending U.S. patent application Ser. No. 10/797,485, filed Mar. 9, 2004, which has been incorporated herein by reference.

As seen in FIG. 1A, guide 30 illustratively comprises first, second and third lumens 31a, 31b and 31c, respectively. The lumens may facilitate passage of endoluminal instruments or tools 40, as well as injection of fluids, introduction of suction, etc. The lumens optionally may comprise seals (not shown). Additional lumens or bores (not shown) may be provided for passage of control wires, rods, etc., that facilitate steering or shape-locking of guide 30 or portions thereof.

Guide 30 also comprises three distinct sections: proximal section 32, middle section 34 and distal section 36. Proximal section 32 may, for example, be compliant, such that the section may assume the profile of the patient's anatomy in which the section is disposed, e.g., the patient's esophagus.

Section 32 optionally may also be shape-lockable when disposed in a desired configuration. Middle section 34 may be steerable and/or able to retroflex in order to position distal section 36 (as well as the distal openings of lumens 31) in proximity to a tissue region of interest. Distal section 36 may also be steerable, for example, in a plane substantially perpendicular to the plane of steering of middle section 34. In this manner, middle section 34 may provide for superior and inferior positioning within a patient's stomach, while distal section 36 provides for anterior and posterior positioning.

Endoluminal instruments or tools 40 are configured for deployment through lumens 31 of steerable guide 30. The tools may, for example, provide endoluminal visualization, grasping, plicating, manipulating, securing and/or affixing of gastric tissue. In FIG. 1, tools 40 illustratively comprise endoscope 42 for visualizing tissue, as well as exemplary tool 44 having end effector 46. End effector 46 may, for example, comprise a tissue grasper, a tissue plicator, a tissue manipulator and/or a tissue affixing or securing element, such as a stapler, a riveter, an anchor delivery and deployment system, a suturing system, etc. Applicant has previously described exemplary instruments or tools configured for coupling to, or advancement through/along, a steerable guide, for example, in co-pending U.S. patent application Ser. No. 10/735,030, filed Dec. 12, 2003, which has been incorporated herein by reference.

Referring now to FIG. 2 in conjunction with FIG. 1A, an example of one method of utilizing apparatus 10 to endoluminally perform gastroplasty via partitioning of a patient's stomach is described. As seen in FIG. 2A, steerable guide 30 is disposed within lumen 21 of sizing tube 20. The sizing tube and guide have been advanced down a patient's esophagus E into the patient's stomach S, either concurrently or sequentially.

Endoscope 42 optionally may be disposed in a lumen 31 of guide 30 to provide visualization, as well as additional steering capabilities, during advancement of tube 20 and guide 30. Furthermore, the endoscope may be advanced into the patient's stomach prior to advancement of steerable guide 30 and sizing tube 20. The steerable guide and sizing tube then may be advanced over the endoscope into the stomach.

Figure 2A:
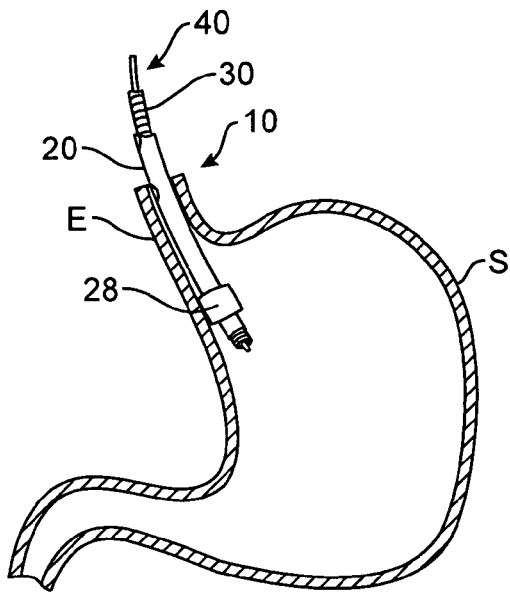
FIGS. 2A-2H are schematic side views, partially in section, illustrating a method of performing endoluminal gastroplasty with the apparatus of FIG. A-1F.
Figure 2B:
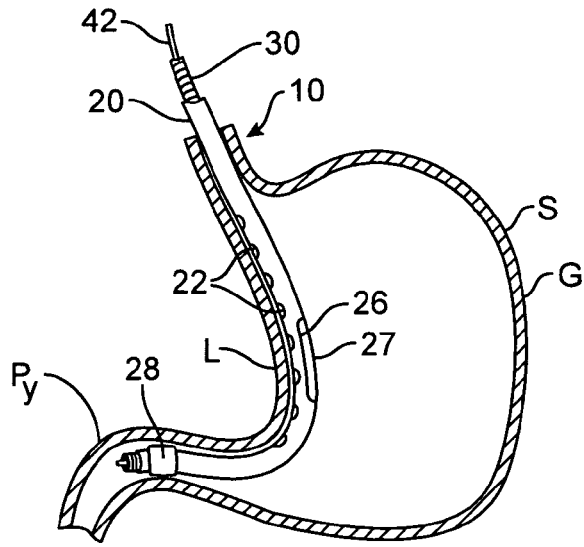

In FIG. 2B, sections 34 and/or 36 of guide 30 (or a distal region of endoscope 42) are steered during further advancement of the guide and sizing tube to position at least a portion of the length of tube 20 in proximity to lesser curvature L of stomach S. Reversible adhering elements 22 of sizing tube 20 may be rotated or positioned to face towards the lesser curvature, while slot 26 of the tube faces greater curvature G. Although adhering elements 22 and slot 26 are shown positioned on opposing sides of sizing tube 20, they may also be positioned at various positions and angles relative to each other over the circumference of sizing tube 20. The tube's distal region preferably is steered in proximity to the patient's pylorus Py.

As an alternative to directly steering guide 30 and sizing tube 20 into position, endoscope 42 may be steered into position prior to advancement of guide 30 and sizing tube 20; the sizing tube and guide then may be advanced over the endoscope. For example, endoscope 42 may be steered such that its distal region is disposed in proximity to the patient's pylorus Py, and at least a portion of its length is disposed in proximity to lesser curvature L. Steerable guide 30 and guiding tube 20 then may be advanced along the endoscope to position the distal region of tube 20 in proximity to the pylorus and at least a portion of the length of tube 20 in proximity to the lesser curvature.

Figure 2C:
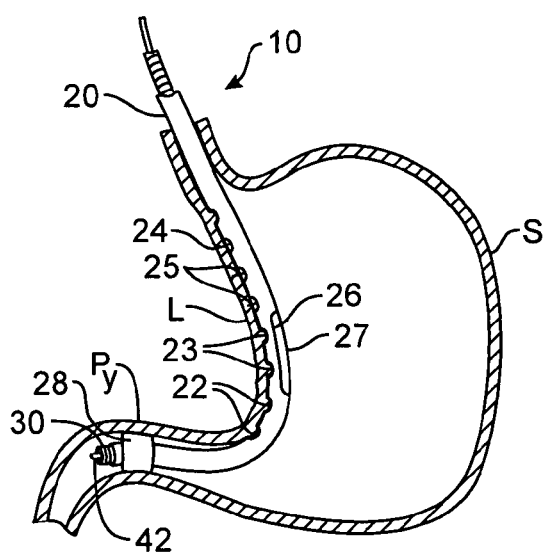

With tube 20 properly positioned, reversible adhering elements 22 may be actuated to reversibly secure the tube along its length, or along a partial length, to the lesser curvature of the patient's stomach, as in FIG. 2C. Actuation may, for example, entail drawing of suction when the elements comprise suction ports 23, or may entail reversible extension of the elements into the wall of stomach S when the elements comprise hooks 24 or barbs 25. Additional adhering elements and/or actuation mechanisms will be apparent to those of skill in the art.

Optional inflatable member 28, e.g. a balloon, also may be inflated to secure the distal region of the tube against the proximal region of a patient's pylorus. Alternatively, inflatable member 28 may be advanced in an uninflated or unexpanded form distally past pylorus Py and then inflated or expanded against a distal region of the pylorus Py. As discussed previously, other types of mechanical anchors may be utilized as an alternative to, or in combination with, inflatable member 28

Figure 2D:
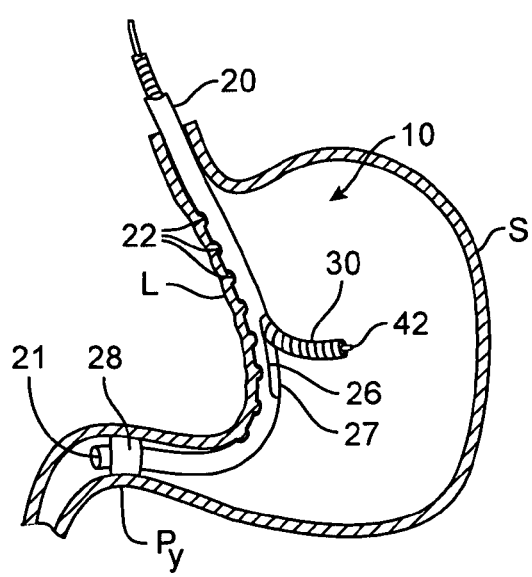
Figure 2E:
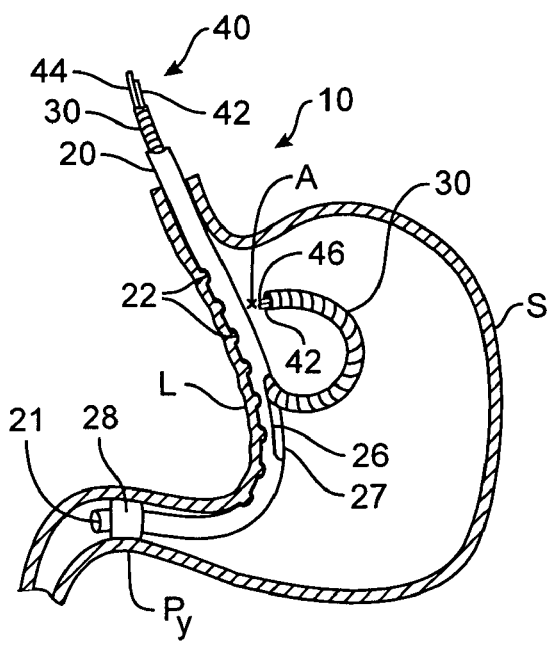

As seen in FIG. 2D, steerable guide 30 may be retracted relative to sizing tube 20, and may be steered such that it exits lumen 21 of sizing tube 20 at side slot 26 and seal 27. Guide 30 is then steered or retroflexed, e.g. via endoscope 42 or via section 34 and/or section 36 of the guide, to reach segments of the patient's stomach superior and/or inferior to slot 26, as in FIG. 2E. In the retroflexed configuration, the distal openings of lumens 31 are directed back towards sizing tube 20. Guide 30 optionally may be reversibly rigidized or shape-locked to maintain the retroflexed configuration, e.g., via tensioning wires disposed within the guide.

After proper superior/inferior positioning, guide 30 may be steered (e.g. via section 36) to grasp, manipulate, plicate, approximate, secure, and/or affix, or otherwise treat, opposing anterior and posterior segments of stomach S via tools 44 advanced through lumens 31 and under visual guidance provided by endoscope 42. The posterior portion of such a secured approximation A is visible in the side-section of FIG. 2E. Advantageously, approximation A may be formed about sizing tube 20 to ensure proper sizing of a partition created in the stomach by the approximation. Thus, the diameter or profile of tube 20 may determine, or aid specification of, the diameter or profile of the partition.

Figure 2F:
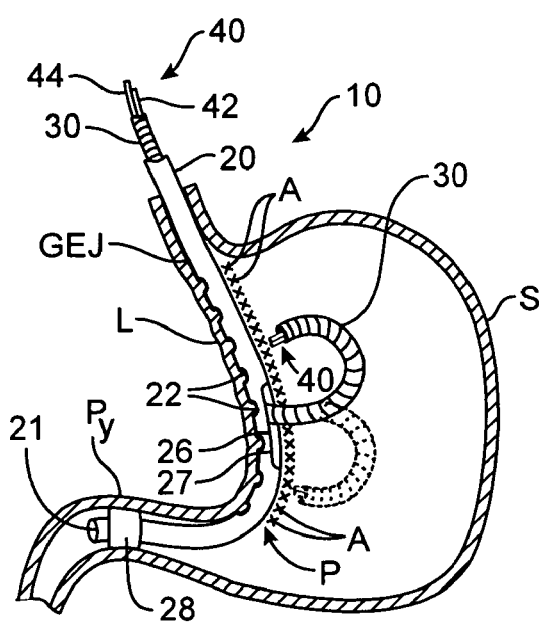

As seen in FIG. 2F, the degree of retroflexing or steering of guide 30, and/or the position of the guide within slot 26 of sizing tube 20, may be altered to change the location and/or orientation of the distal end of guide 30 at different levels within the superior-inferior plane of the patient's stomach for formation of further approximations A of opposing tissue segments about tube 20. Likewise, as seen in dotted profile, the guide may be retroflexed from superior to inferior, and vice versa, to extend the reach of the guide and to form approximations inferior or distal to slot 26. The spacing of approximations A may be about 1 cm, though alternative spacing(s) may be provided.

Visual markings or other indicators optionally may be provided on sizing tube 20 to map out and/or facilitate proper spacing of the approximations. Applicant has previously described methods and apparatus for mapping out formation of such approximations during creation of an endoluminal pouch, for example, in co-pending U.S. patent application Ser. No. 10/797,910, filed Mar. 9, 2004, which is incorporated herein by reference in its entirety.

As can be seen in FIG. 2F, a pouch P is formed within stomach S just inferior to the patient's gastroesophageal junction GEJ upon formation of a plurality of approximations A about sizing tube 20. The profile or diameter of sizing tube 20 may determine, or aid specification of, the profile of pouch P and facilitate proper sizing of the pouch. The pouch partitions or reduces the stomach and restricts the passage of food by directing food through the pouch and bypassing a significant portion of the patient's stomach. The pouch also may effectively form a Vertical Banded Gastroplasty or Magenstrasse and Mill in an endoluminal fashion.

Additional illustrative methods and apparatus for forming an endoluminal pouch with tools deployed via a steerable guide (including methods and apparatus for forming and securing approximations A) are described, for example, in Applicant's co-pending U.S. patent application Ser. No. 10/735,030, filed Dec. 12, 2003, which has been incorporated herein by reference. Aspects of the methods and apparatus described in that reference may be incorporated into, or used in combination with, the methods and apparatus described herein.

Figure 2G:
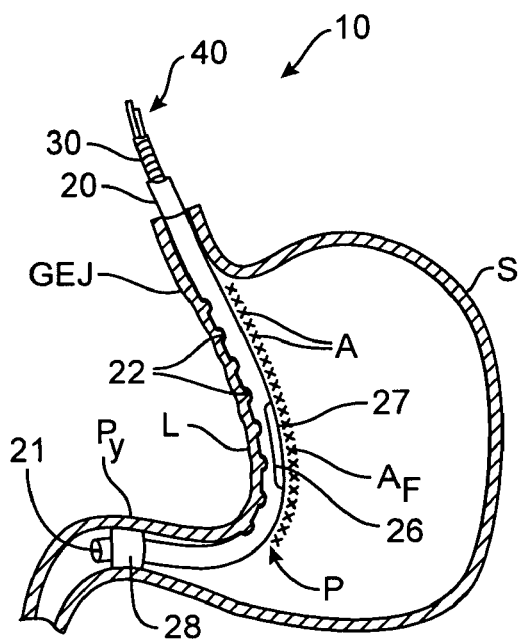

During or after formation of pouch P, steerable guide 30, as well as any instruments or tools 40, may be retracted within lumen 21 of sizing tube 20 for removal from the patient, as in FIG. 2G. Final formation of pouch P, e.g., formation of a final approximation $A_F$ at the location where guide 30 had exited slot 26 of sizing tube 20, optionally may be achieved after the guide has been returned to lumen 21 of the sizing tube. For example, approximation $A_F$ may be formed by tightening sutures or anchors that were placed prior to returning guide 30 to the lumen of tube 20.

Figure 2H:
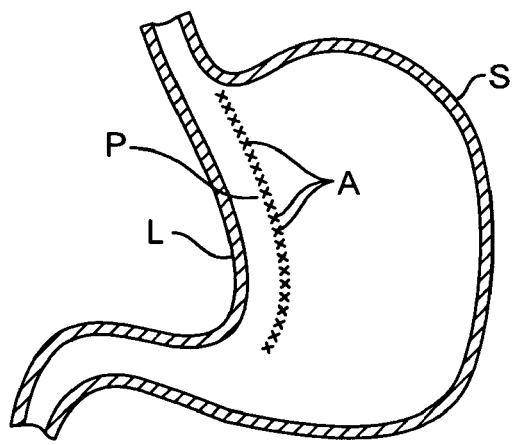

At any time during or after formation of pouch P, inflatable member 28 of sizing tube 20 may be deflated to decouple tube 20 from the patient's pylorus Py, and/or reversible adhering elements 22 may be removed from lesser curvature L of stomach S. As seen in FIG. 2H, after member 28 has been deflated and elements 22 have been removed, sizing tube 20, as well as guide 30 and tools 40, may be removed from the patient to complete endoluminal formation of pouch P. Thereafter, the partition provided by pouch P regulates the passage of food through stomach S to promote weight loss.

Figure 3:
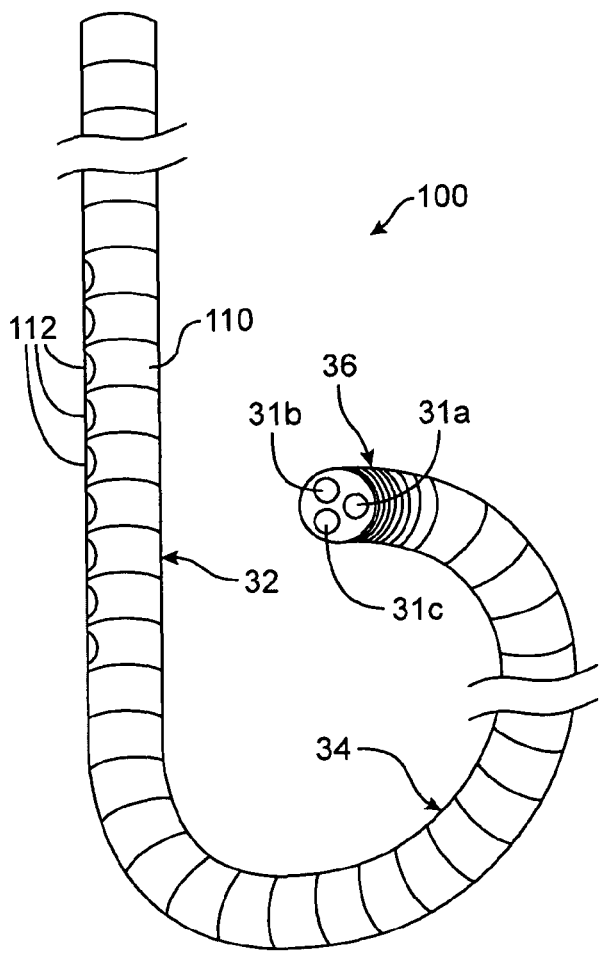
FIG. 3 is a schematic side view of another variation of the apparatus.

Referring now to FIG. 3, another variation of the apparatus is described. Apparatus 100 comprises steerable guide 110 having reversible adhering elements 112 disposed along at least a portion of its length. Guide 110 may comprise multiple lumens and/or multiple sections, and illustratively comprises previously described lumens 31 and previously described sections 32, 34 and 36. Reversible adhering elements 112 illustratively are disposed along section 32 of the guide. Sections 32, 34 and 36 of guide 110 may comprise varying capacities for steering, shape-locking or rigidizing, retroflexing, etc. Endoluminal instruments or tools 40, such as previously described endoscope 42 and exemplary tool 44, may be advanced along or through steerable guide 110, e.g., through lumens 31, or may be coupled thereto.

By providing steerable guide 110 with reversible adhering elements 112, apparatus 100 mitigates a need for a separate sizing tube. Rather, as described hereinbelow with respect to FIG. 4, section 32 of the guide may engage, for example, the lesser curvature of a patient's stomach, while sections 34 and 36 are used to steer and position a more distal portion of the guide for formation of an endoluminal pouch. Advantageously, in order to facilitate proper sizing of such a pouch, the pouch may be formed about section 32 of the guide while that section is coupled to the patient's lesser curvature. Thus, the diameter or profile of section 32 may facilitate formation of the endoluminal pouch with a specified profile or diameter.

Steerable guide 110 may have a maximum diameter of less than or equal to about 40 Fr. Preferably, the guide may have a maximum diameter of between about 26 Fr and 40 Fr, and more preferably may have a diameter between about 30 Fr and 36 Fr. Optionally, the diameter of guide 110 may vary along its length. Visual markings or other indicators may be provided along section 32 guide 110 to map out or facilitate proper spacing of approximations formed during creation of an endoluminal pouch about section 32.

With reference to FIG. 4, a method of using apparatus 100 to perform endoluminal gastroplasty is described. In FIG. 4A, apparatus 100 is advanced down a patient's throat through esophagus E into stomach S, for example, under visual guidance provided by endoscope 42 and/or along the endoscope. Apparatus 100 may, for example, be advanced concurrently with endoscope 42, or the apparatus may be advanced over the endoscope after a distal region of the endoscope has been disposed within the patient's stomach. A combination of these approaches, as well as alternative approaches, also may be utilized to properly position apparatus 100.

Once disposed within the stomach, steerable guide 110 of apparatus 100 is steered such that section 32 of the guide is disposed in proximity to lesser curvature L of the patient's stomach. Reversible adhering elements 112 are then actuated to reversibly couple section 32 of the guide to the lesser curvature, as in FIG. 4B.

Figure 4A:
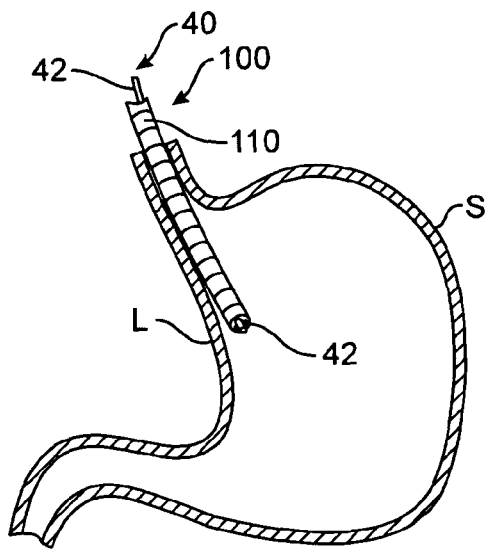
FIGS. 4A-4D are schematic side views, partially in section, illustrating a method of performing endoluminal gastroplasty with the apparatus of FIG. 3.
Figure 4B:
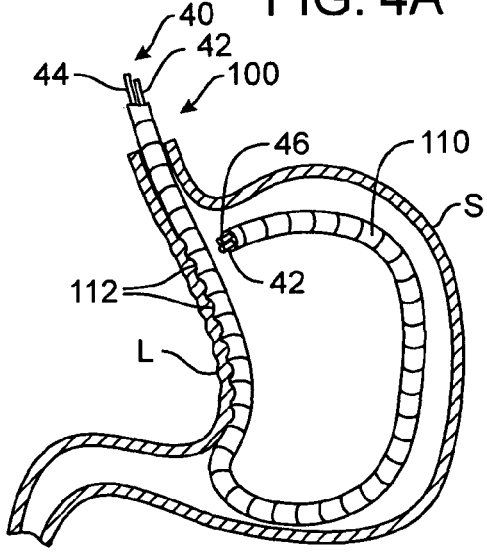
Figure 4C:
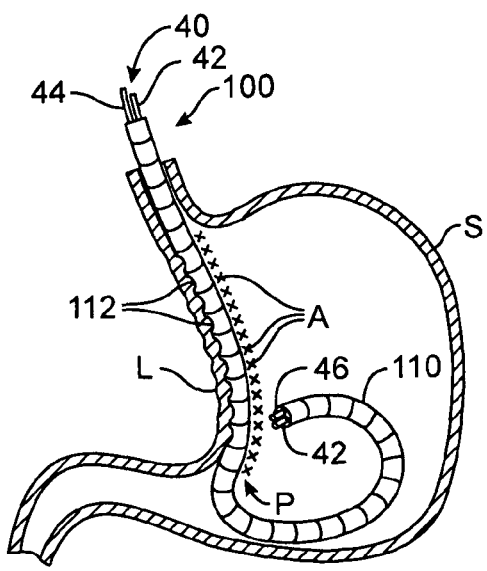
Figure 4D:
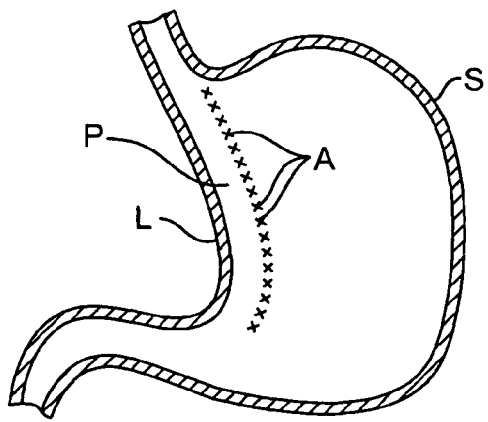

As seen in FIG. 4C, guide 110 is then steered, retroflexed, shape-locked, rigidized and/or otherwise maneuvered to form a plurality of approximations A about section 32 of the guide, thereby creating pouch P. The approximations and pouch may, for example, be formed via tools 44 deployed through lumens 31 of the guide under visual guidance from endoscope 42. Advantageously, by forming pouch P about section 32 of guide 110, which is reversibly adhered to lesser curvature L of stomach S, a specified sizing or profile of the pouch may be achieved. In FIG. 4D, elements 112 may be removed from the lesser curvature of the patient's stomach, and apparatus 100, as well as any tools 40, may be removed from stomach S and pouch P, thereby completing endoluminal gastroplasty. Thereafter, pouch P regulates the passage of food through stomach S to promote weight loss.

Although various illustrative embodiments are described above, it will be evident to one skilled in the art that various changes and modifications are within the scope of the invention. It is intended in the appended claims to cover all such changes and modifications that fall within the true spirit and scope of the invention.

What is claimed is:

1. A system for endoluminally performing gastroplasty, comprising:
   a sizing tube for endoluminal passage through a patient's esophagus into the patient's stomach, the sizing tube having a plurality of reversible adhering elements, at least one reversible adhering element comprising a suction port, a sizing tube lumen extending at least partially through the sizing tube, and at least one side port in the sizing tube:
   a steerable guide for insertion within the sizing tube lumen and out through the side port, with the steerable guide having at least one control wire to facilitate steering, and with the steerable guide having at least one tool lumen to allow movement of an endoscopic tool through the steerable guide; and
   a first endoluminal tool extendable through the tool lumen, the first endoluminal tool comprising a tissue grasper and a tissue anchor delivery system.

2. The system of claim 1 wherein the sizing tube is configured to engage a lesser curvature of the patient's stomach with the at least one reversible adhering element.

3. The system of claim 1. wherein the sizing tube further comprises a mechanical anchor comprising an inflatable member located adjacent to a front end of the sizing tube.

4. The system of claim 1 with the sizing tube further comprising a seal for sealing the at least one side port.

5. The system of claim 1, further comprising a second endoluminal tool extendable through the tool lumen and configured to perform at least one or more of tissue visualization, tissue grasping, tissue plication, tissue manipulation, tissue approximation, tissue securing, tissue treatment and combinations thereof.

6. The system of claim 1, wherein the steerable guide comprises multiple sections.

7. The system of claim 6, wherein the multiple sections comprise varying capacities for performing tasks chosen from the group consisting of steering, rigidizing, shape-locking, retroflexing and combinations thereof.

8. The system of claim 1, wherein the adhering elements are substantially aligned in a row on the sizing tube.

9. The system of claim 1, wherein the adhering elements are spaced in a staggered pattern on the sizing tube.

10. The system of claim 1 wherein the adhering elements are positioned on an opposing side of the sizing tube with respect to the side port.

11. The system of claim 1 wherein the adhering elements are positioned at an angle about the circumference of the sizing tube with respect to the side port.

12. A method for endoluminally performing gastroplasty, comprising:
    advancing a sizing tube down a patient's throat into the patient's stomach;
    reversibly adhering a curved sidewall of the sizing tube to the patient's stomach with a plurality of reversible adhering elements, at least one reversible adhering element comprising a suction port;
    endoluminally forming a pouch around the sizing tube by steering a steerable guide in at least two dimensions to form multiple approximations of opposing anterior and posterior portions of the stomach around the sizing tube at different levels within the superior-inferior plane of the patient's stomach, with the sizing tube assisting in determining a dimension of the pouch, and with the steerable guide comprising a tissue grasper and a tissue anchor delivery system; and
    removing the sizing tube from the patient.

13. The method of claim 12, wherein advancing a sizing tube further comprises advancing a steerable guide with an integrated sizing tube.

14. The method of claim 12, wherein advancing a sizing tube further comprises advancing the sizing tube while the steerable guide is disposed within a lumen of the sizing tube.

15. The method of claim 14, wherein endoluminally forming a pouch about the sizing tube further comprises: passing the steerable guide from the lumen of the sizing tube through a side port of the sizing tube; steering the guide within the patient's stomach; advancing tools through or along the guide; and endoluminally forming the pouch with the tools.

16. A system for endoluminally performing gastroplasty, the system comprising:
    a steerable guide having a plurality of reversible adhering elements, with at least one reversible adhering element comprising a suction port, disposed along a length thereof for engaging a lesser curvature of a patient's stomach; and
    at least one endoluminal tool comprising a tissue grasper and a tissue anchor delivery system advanceable through or along the steerable guide.

17. The system of claim 16, wherein the steerable guide further comprises multiple sections, the multiple sections comprising: a first section having the plurality of reversible adhering elements for engaging the lesser curvature; and at least one additional section that is steerable to facilitate formation of an endoluminal pouch about the first section within the patient's stomach via the endoluminal tool.

18. A system for endoluminally performing gastroplasty comprising:
    a sizing tube having a plurality of reversible adhering elements, at least one reversible adhering element comprising a suction port, a lumen extending at least partially through the sizing tube, and at least one side port in the sizing tube;
    a steerable guide configured for insertion within the lumen and passage through the side port, with the steerable guide having multiple sections to allow the steerable guide to steer, retroflex, rigidize, or shape-lock, or a combination of them; and
    at least one endoluminal tool comprising a tissue grasper and a tissue anchor delivery system advanceable through or along the steerable guide.

19. The system of claim 18, with the steerable guide having at least one control wire to facilitate steering.

20. A system for endoluminally performing gastroplasty, comprising:
    a sizing tube for endoluminal passage through a patient's esophagus into the patient's stomach, the sizing tube having at least one reversible adhering element comprising a suction port, a sizing tube lumen extending at least partially through the sizing tube, at least one side port in the sizing tube, and a mechanical anchor comprising an inflatable member located adjacent to a front end of the sizing tube;
    a steerable guide for insertion within the sizing tube lumen and out through the side port, with the steerable guide having at least one control wire to facilitate steering, and with the steerable guide having at least one tool lumen to allow movement of an endoscopic tool through the steerable guide; and
    a first endoluminal tool extendable through the tool lumen, the first endoluminal tool comprising a tissue grasper and a tissue anchor delivery system.

21. The system of claim 20 wherein the sizing tube is configured to engage a lesser curvature of the patient's stomach with the at least one reversible adhering element.

22. The system of claim 20 with the sizing tube further comprising a seal for sealing the at least one side port.

23. The system of claim 20, further comprising a second endoluminal tool extendable through the tool lumen and configured to perform at least one or more of tissue visualization, tissue grasping, tissue plication, tissue manipulation, tissue approximation, tissue securing, tissue treatment and combinations thereof.

24. The system of claim 20, wherein the steerable guide comprises multiple sections.

25. The system of claim 24, wherein the multiple sections comprise varying capacities for performing tasks chosen from the group consisting of steering, rigidizing, shape-locking, retroflexing and combinations thereof.

26. The system of claim 20 wherein the sizing tube further comprises a plurality of additional reversible adhering elements.

27. The system of claim 26, wherein the adhering elements are substantially aligned in a row on the sizing tube.

28. The system of claim 26, wherein the adhering elements are spaced in a staggered pattern on the sizing tube.

29. The system of claim 20 wherein the adhering elements are positioned on an opposing side of the sizing tube with respect to the side port.

30. The system of claim 20 wherein the adhering elements are positioned at an angle about the circumference of the sizing tube with respect to the side port.

* * * * *